United States Patent [19]

Ginsburg

[11] Patent Number: 5,180,364
[45] Date of Patent: Jan. 19, 1993

[54] VALVED SELF-PERFUSING CATHETER GUIDE

[76] Inventor: Robert Ginsburg, 2489 Alpine Rd., Menlo Park, Calif. 94025

[21] Appl. No.: 725,694

[22] Filed: Jul. 3, 1991

[51] Int. Cl.$^5$ .................. A61M 31/00; A61M 5/00
[52] U.S. Cl. .................. 604/53; 604/247; 604/280; 128/658
[58] Field of Search .................. 128/656–658; 604/99, 51–53, 264, 280, 244–247, 167, 169

[56] References Cited

U.S. PATENT DOCUMENTS

| | | | |
|---|---|---|---|
| 3,726,283 | 4/1973 | Dye et al. | 604/247 X |
| 3,788,328 | 1/1974 | Alley et al. | 604/178 |
| 3,995,617 | 12/1976 | Watkins et al. | 604/247 X |
| 4,014,317 | 3/1977 | Bruno | 604/247 X |
| 4,246,932 | 1/1981 | Raines | 137/512 |
| 4,540,402 | 9/1985 | Aigner | 604/44 |
| 4,661,094 | 4/1987 | Simpson | 604/53 |
| 4,701,166 | 10/1987 | Groshong et al. | 604/247 |
| 4,705,501 | 11/1987 | Wigness et al. | 604/43 |
| 4,769,005 | 9/1988 | Ginsburg et al. | 604/53 |
| 4,804,358 | 2/1989 | Karcher et al. | 600/17 |
| 4,857,054 | 8/1989 | Helfer | 604/102 |
| 4,892,095 | 1/1990 | Nakhgevany | 128/207.14 |
| 4,892,519 | 1/1990 | Songer et al. | 604/96 |
| 4,909,252 | 3/1990 | Goldberger | 606/194 |
| 4,976,691 | 12/1990 | Sahota | 604/96 |
| 4,995,863 | 2/1991 | Nichols et al. | 604/247 |
| 5,030,210 | 7/1991 | Alchas | 604/247 |
| 5,112,301 | 5/1992 | Fenton, Jr. et al. | 604/30 |

Primary Examiner—John D. Yasko
Assistant Examiner—Adam J. Cermak
Attorney, Agent, or Firm—Townsend and Townsend

[57] ABSTRACT

Valved self-perfusing guiding catheter comprises an elongate, flexible catheter body, passageways disposed along at least a portion of the catheter body for permitting perfusion through a central lumen of the catheter body, and one-way valves for preventing passage of injectable agents, such as contrast media, through the passageways.

22 Claims, 7 Drawing Sheets

VALVED SELF-PERFUSING CATHETER GUIDE

BACKGROUND OF THE INVENTION

The present invention relates generally to apparatus and methods for inserting vascular catheters into blood vessels and, more particularly, to the construction and use of a guiding catheter for selectively directing such catheters to particular blood vessels.

A wide variety of non-invasive angioplastic methods exist for removing obstructions from blood vessels. Generally, these methods rely on the peripheral introduction of a catheter to the site of the obstruction and the manipulation of the catheter in some manner to remove the obstruction. The most common method employs a balloontipped catheter which is inflated at the site of the obstruction to dilate the passage therethrough. Also, laser catheters are used to ablate obstructions, and certain catheters are then provided with cutting implements to excise the obstructions.

One difficulty with such angioplastic techniques has been the ability to properly locate a catheter within the patient's vascular system. A common approach to this problem is to place the catheter with a steerable guidewire. Typically, the guidewire includes a spring tip which is bent so that the direction of insertion can be selected by rotating the wire. The catheter, which includes a central or guidewire lumen, is then inserted over the guidewire to the proper location. Alternatively, some catheters have an integral spring tip which is used to guide the catheter in an analogous manner.

Not all catheters are well suited for placement using guidewire techniques however. Some angioplasty catheters and other therapeutic modalities (e.g., fluted cutters), for example, lack a guidewire lumen. Since these devices cannot accommodate a guidewire, they must be placed using other techniques.

Alternate means for positioning vascular catheters are known. For example, special catheter have been devised for positioning vascular catheters and other therapeutic modalities within a particular vessel. These guiding catheters or catheter guides typically include a central lumen which accommodates a vascular catheter. In operation, the guide is first positioned within the vessel of interest, typically with the aid of fluoroscopy. The central lumen of the guide is often used for injecting contrast media so that the lesion of the vessel may be concurrently visualized. Once the guide is properly positioned, a therapeutic catheter may be readily advanced to the lesion by passing it through the central lumen.

Other means for positioning vascular catheters are known. U.S. Pat. No. 4,769,005, for example, describes a guiding sheath for inserting guidewires or vascular catheters within a blood vessel which includes an elongate body having a plurality of axial lumens. The insertional sheath includes a primary axial lumen which is used for inserting the sheath onto a guidewire to locate where a branch in the vascular system occurs. Under fluoroscopic guidance, the sheath is positioned so that one of the lumens is properly located to direct the guidewire or catheter in the desired direction. U.S. Pat. No. 4,405,314 also describes an insertional catheter which provides for selective insertion of catheters into arteries.

The use of positioning devices, such as catheter guides and the like, incurs a significant penalty however. Due to their relatively large size, these devices often impede blood flow through the vessels in which they are inserted. For example, guiding catheters used for coronary angioplasty often impede blood flow through the ostium of a coronary artery.

The problem of maintaining blood flow (and hence preventing ischemia) with guiding catheters has been largely solved by adding side holes which allow self-perfusion of the vessel. This solution, however, has created another problem. While self-perfusing guides function well to maintain blood flow, they are poorly adapted for angiography techniques because large amounts of contrast media are typically lost to the surrounding vasculature. In particular, it is desirable to deliver contrast media through the distal end of the guide, which is positioned proximate a lesion; delivery of contrast media to other locations serves only to interfere with angiography.

With prior art guiding catheters, contrast media preferentially exits through the perfusion holes during its injection. Thus, a significant if not substantial amount of contrast media is delivered to a vessel which is not of particular interest (e.g., contrast media is delivered to the aorta during imaging of coronary arteries). As a result, the angiographic image is degraded, the risk of contrast toxicity is increased, and expensive contrast media is wasted. All three factors combine to greatly increase the overall cost and morbidity of using catheter guides.

Thus, it is highly desirable to provide apparatus and methods for the improved placement of vascular catheters and the like within the vascular system without increased risks from ischemia or excess contrast media. In particular, it is desirable to provide a guiding catheter which can facilitate the positioning of catheters to specific branches within the vascular system with the aid of angiographic techniques; concurrently, the guiding catheter should maintain perfusion while preventing loss of contrast media. Additionally, it is desirable to provide a guiding catheter which can stent a vessel. Particularly, when a dissection or flap occurs within a vessel (e.g., left main or proximal coronary artery), the catheter should be able to be placed in the area of disruption to permit continual perfusion of the distal vascular bed (temporary stent) until more definitive therapy can be undertaken. The present invention fulfills this and other needs.

SUMMARY OF THE INVENTION

According to the present invention, apparatus and methods are provided for directionally inserting vascular catheters and other therapeutic modalities within desired vessels. While the invention is particularly useful when employed in a patient's coronary vasculature, the invention will also find application in other vessels (e.g, renal arteries, venae cava, thoracic duct, and the like) or luminal structures (e.g., urethra, biliary tree, and the like).

The apparatus of the present invention is a guiding catheter which includes an elongated body having at least one lumen extending therethrough. Proximate one end of the elongated body, typically (although not necessarily) the distal end, a plurality of valved passageways are provided.

Each valved passageway or perfusion means acts as a one-way valve. During injection through the inner lumen the valves close so that the injected agent (e.g., contrast media) is not lost to the surrounding vasculature. When the catheter is not being injected (i.e., passive mode), however, surrounding hydrostatic (blood) pressure opens each valve allowing blood to perfuse through the passageways.

In a method of the present invention, the guiding catheter is percutaneously introduced to the patient's vascular system, typically employing conventional J-wire technique. The guide is then rotationally and translationally advanced to a desired location. Upon placement, blood passes through the valved passageways of the catheter, thereby maintaining blood flow past the distal end of the catheter. A second catheter (or other therapeutic modality) is then inserted into the guiding catheter and advanced to a desired location with the vessel of interest.

DESCRIPTION OF THE SPECIFIC EMBODIMENT(S)

Figure 1A:
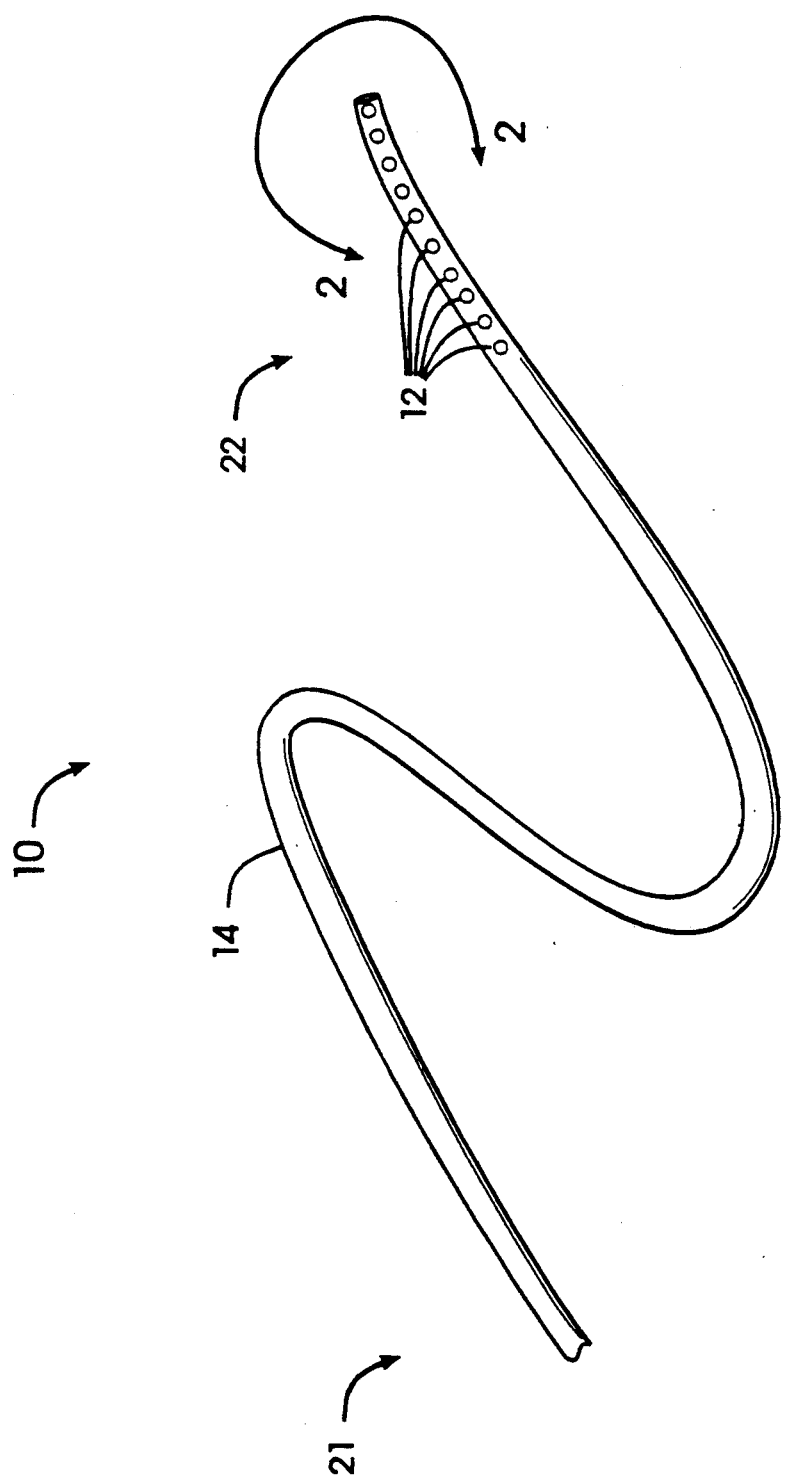
FIG. 1A is a side view of a valved self-perfusing guiding catheter of the present invention.

The present invention is useful for guiding a wide variety of catheters and guidewires for treating vascular lesions, for example, stenotic or thrombotic lesions. The present invention is particularly useful when employed in regions which are difficult to position a vascular catheter, such as the coronary arteries.

The catheter of the present invention comprises an elongate, flexible catheter body having proximal and distal ends. The length and diameter of the catheter body varies depending on the intended application, typically having a length and a range from about 30 cm to 150 cm and a diameter in the range from 7 French to 21 French (1 French is equal to 0.33 mm). For reaching coronary blood vessels, the catheter body will typically have a length of about 100 cm and a diameter in the range from about 7 French to 11 French. When it is intended to reach peripheral blood vessels, the catheter body will typically have a length from about 30 cm to 100 cm and a diameter from about 7 French to about 21 French.

The catheter body may include one or more tubular elements within multiple tubes, usually co-axially arranged. The tubes will typically be formed by extrusion of an organic polymer, typically a thermoplastic such as nylon, polyurethane, polyethylene terephthalate (PET), polyvinyl chloride (PVC), polyethylene, or the like. The tubes may be reinforced or unreinforced, with reinforcement provided by metal wires, metal braided cables, or the like. Processes and techniques for forming intravascular catheter bodies are well known in the art and well described in the patent, scientific, and medical literature.

The tubes may define one or more lumens which originate at the proximal end of the catheter body and extend axially therethrough. At least one lumen (e.g., a central lumen) is provided for guiding a vascular catheter or the like from the proximal end of the catheter body to its distal end. Also, the lumen transports injectable agents (e.g., drug or contrast media) for the proximal end to the distal end. Additional lumens may be provided for a variety of purposes, for example, to allow introduction and placement of additional guidewires, catheters, or the like.

The catheter of the present invention includes passageways along at least a portion of the catheter body, typically (although not necessarily) disposed towards the distal end. The passageways, which may be in the form of holes (e.g., circular or oval passageways), slits (elongate openings), vents, or the like, provide selective communication between the central lumen and a region external to the catheter The passageways are provided with means for restricting flow to one direction. In a particular embodiment, each passageway is provided with a one-way valve. During injections of agents through the central lumen, the valves occlude the passageways so that the contents of the central lumen (e.g., contrast media) may not pass through. That is, the valves close in response to higher relative pressures that occur in the central lumen during injection. After an injection, however, the valves open as a result of relatively lower intraluminal pressure (i.e., lower than surrounding blood pressure).

In one embodiment, each valve comprises a valve leaflet attached to the inner wall of the catheter body proximate a passageway. Each leaflet is formed of plastic, metal, or other material which may serve to occlude a passageway. In a preferred embodiment, each leaflet is formed of a thin skirt of plastic such as mylar. The leaflets may be attached using means known in the art, including welding, brazing, bonding, gluing, or securing with fasteners (e.g., hinges or pins). The attachment of the leaflet may be coupled with a tension means, such as a spring or pressure plate, so that the leaflet defaults to a particular position (e.g., open position for use in the venous system).

In an alternative embodiment, each valve leaflet is secured to the outer wall of the catheter body proximate a passageway. In this embodiment, the outer wall includes an indentation proximate each passageway for accommodating a valve leaflet. Each valve leaflet is secured at its proximal end with its distal end extending through a corresponding passageway so that the valve will be forced closed in response to relatively higher intraluminal pressures.

Those skilled in the art will appreciate that many structural alternatives can serve as the valve means, and the present invention is not restricted to any particular one. For example, the valve means may comprise a caged ball, a caged disc, multi-cuspid valve, or the like.

Referring now to FIGS. 1-5, the construction of guiding catheters in accordance with the principles of the present invention will be described. Referring to FIG. 1A, a first exemplary catheter 10 comprises a catheter body 14 having a proximal end 21 and a distal end 22. The catheter body 14 comprises a single flexible tubular member with a central lumen 16 extending from proximal end 21 to distal end 22.

The proximal end 21 of catheter body 14 is selectively connectable to an injectable source (e.g., a syringe or I.V. tubing). In particular, the proximal end 21 is adapted to receive a luer adapter or similar connector means. The proximal end 21 is also adapted to deliver a second catheter to the central lumen 16. If the guiding catheter 10 is to include additional lumens, the proximal end 21 may be adapted to accommodate a proximal housing having one or more ports for accessing the lumens.

Catheter 10 includes passageways 12 along at least a portion of body 14. The passageways may be disposed along any portion of catheter 10. To prevent occlusion, e.g., by a vessel wall or a balloon surface, the passageways 12 should be provided at a plurality of locations. If the passageways are disposed towards the distal end, however, the perfused fluid (e.g., blood) will travel less distance before reaching the distal end 22. The passageways may be any type of opening, such as holes, slits, vents, and the like which afford communication between the central lumen 16 and a region exterior to the catheter 10. In the embodiment of FIG. 1A, the passageways 12 comprise a plurality of side holes, typically circular, each of which is radially located at a preselected distance relative to its neighbor.

Figure 1B:
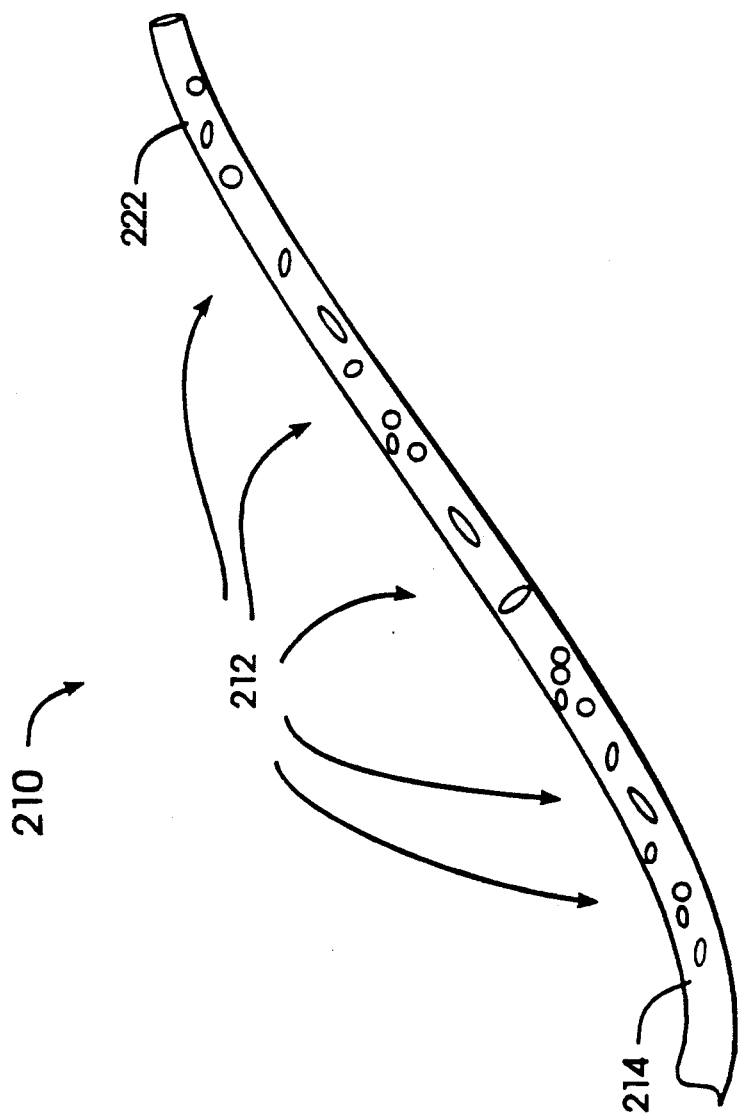
FIG. 1B is a side view of an alternative embodiment of the present invention, the view showing only the distal end of the catheter.

In a guide 210 of FIG. 1B, however, the passageways 212 comprise a plurality of holes of any shape, size, and position along the distal end 222 of the catheter body 214. Thus, the passageways may also be random in configuration as well as location.

Figure 2:
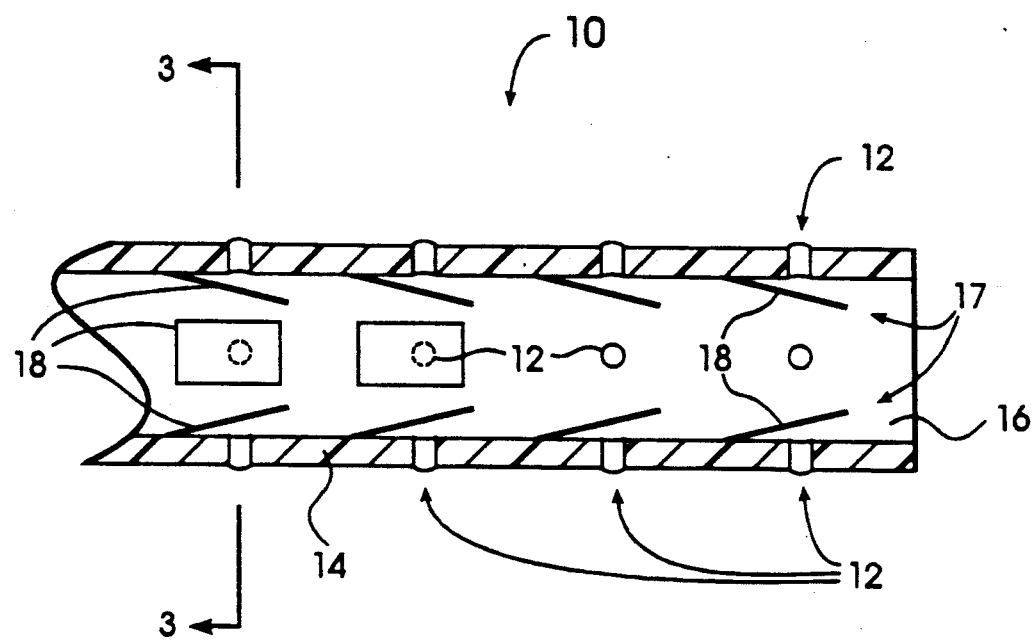
FIG. 2 is a longitudinal sectional view of a portion of the catheter indicated by line 2—2 of FIG. 1A.
Figure 3:
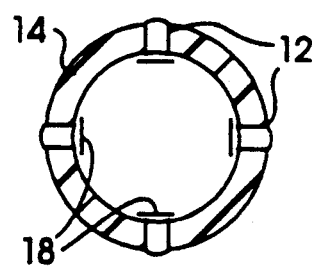
FIG. 3 is a cross-sectional view of a portion of the catheter indicated by line 3—3 of FIG. 2.

Referring to FIGS. 2-3, the passageways 12 are provided with means for restricting flow to one direction. In a preferred embodiment, each passageway is provided with a valve means 17 which operates as a one-way valve. As shown, each valve 17 includes a leaflet 18 secured to the inner wall of tube 14 at a location proximate a passageway 12. Valve leaflet 18 may be secured in any conventional manner, e.g., welding, bonding, brazing, adhesives, gluing, fasteners, or the like. Alternatively, valve leaflets 18 may be formed from a separate laminate structure (not shown) disposed co-axially within the central lumen 16. In this alternative construction, the laminate structure need only extend a region sufficient to cover the plurality of passageways 12.

Referring now to FIGS. 4-7, the structure and function of the valve leaflets 18 will be further described. Each valve leaflet 18 includes a proximal end 18a and distal end 18b. Each leaflet is secured to the catheter body 14 by its proximal end 18a so that the leaflet flexes or pivots about its proximal end. The distal end 18b, on the other hand, is not attached and is oriented towards the distal end 22 of the catheter.

Figure 4:
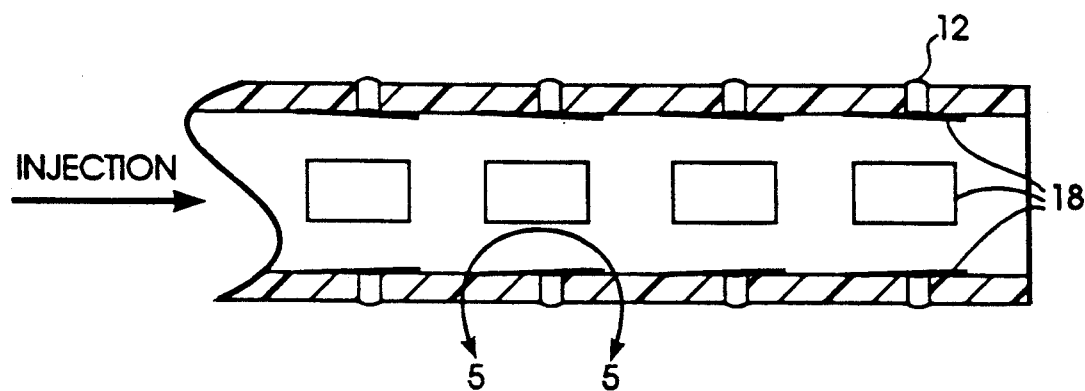
FIG. 4 is the catheter portion from FIG. 2, the valves being shown in a closed position.
Figure 5:
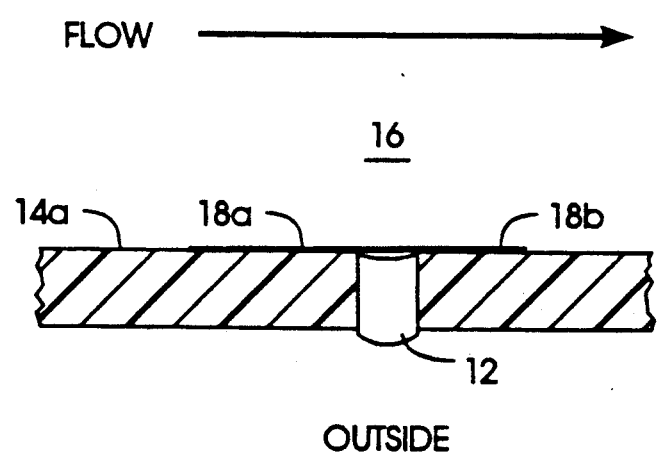
FIG. 5 is a detailed, sectional view of a valve of FIG. 4 indicated by line 5—5.

Each valve means 17 and passageway 12 pair operates as follows. When a relatively higher pressure exists within the central lumen 16, the leaflets 18 occlude the passageways 12 (as shown in FIG. 4). In this case, the higher intraluminal pressure forces the leaflet 18 into apposition with the inner wall 14a of the catheter body 14, thereby closing the passageway 12. In particular, the leaflet 18 flexes or pivots about its proximal attachment 18a to bring its distal end 18b into contact with the inner wall. This situation typically occurs during injection into the central lumen 16, e.g., with contrast media.

Figure 6:
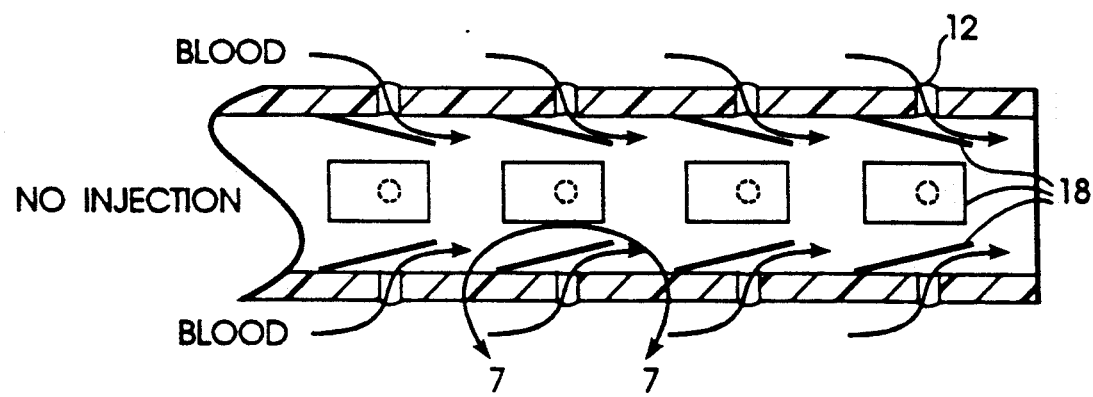
FIG. 6 is the catheter portion from FIG. 5, the valves being shown in an open position.
Figure 7:
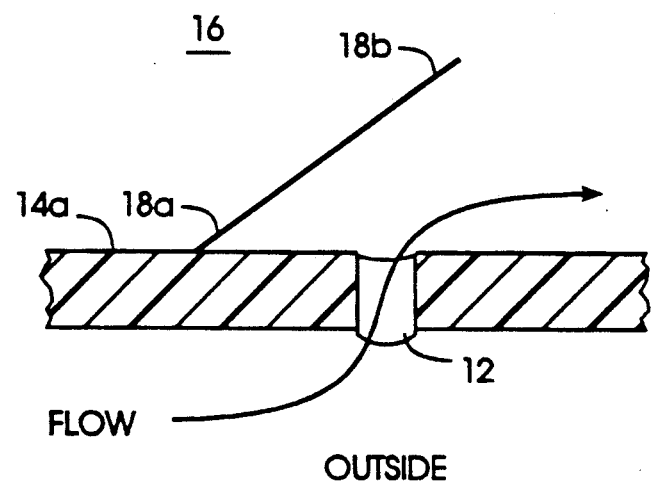
FIG. 7 is a detailed, sectional view of a valve of FIG. 6 indicated by line 7—7.

Referring now to FIGS. 6-7, the complementary situation is illustrated. In response to relatively higher outside or external pressure (blood pressure), leaflet 18 is forced away from its apposition against passageway 12. In particular, when there is no injection within central lumen 16, leaflet 18 flexes or pivots about its proximal end 18a so that the distal end 18b is distracted from its contact with the inner wall 14a. Typically, the relatively higher external pressure results from the blood pressure present within the vessel. As shown, a portion of the blood flow is diverted from an exterior region, through the passageways 12, and into the central lumen 16. From here, the flow is directed towards the distal end 22 of the catheter for delivery to the vessel at a location distal to the catheter 10.

Figure 8:
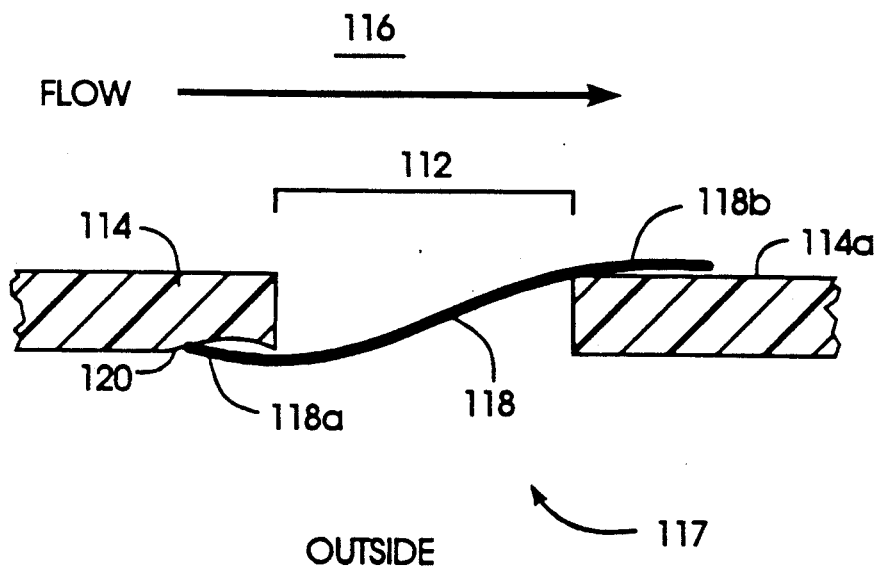
FIG. 8 is a detailed, sectional view of an alternate valved passageway.
Figure 9:
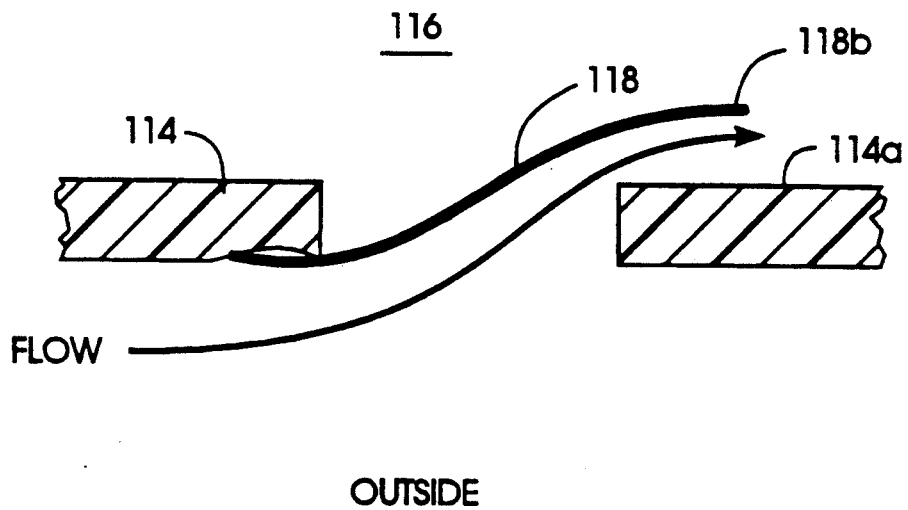
FIG. 9 illustrates the valved passageway of FIG. 8 in an open position.

Referring now to FIGS. 8-9, an alternative embodiment of the passageway and valve means is shown. Catheter body 114 is provided with a plurality of passageways, such as the passageway 112. At a proximate end of each passageway 112, catheter body 114 includes an indentation or recess 120 along its exterior surface. Secured to the catheter body 114 at indentation 120 is valve means 117. Valve means 117 comprises a valve leaflet 118 having a proximal end 118a which is secured to the indentation 120 and a distal end 118b which is free. Leaflet 118 may be secured to the catheter body 114 using conventional means such as those described hereinabove for leaflet 18. The valve leaflet 118, like leaflet 18, is flexible or pivotable at or near its proximal end 118a. Tension means (not shown), such as a spring, pressure plate, or the like, may be coupled to the leaflet 118 (or 18) to urge the valve into a default position.

As shown in FIG. 8, when the valve 117 is closed, it blocks the passageway 112. This typically occurs in response to relatively higher pressures within a central lumen 116, such as those that occur during injection of contrast media. In particular, the increased intraluminal pressure forces the distal end 118b of the valve against the inner wall 114a of the catheter body, thus blocking communication between the central lumen 116 and a region exterior to the catheter.

In response to relatively higher outside or external pressure, e.g., when no contrast media (or the like) is being injected within the central lumen 116, the valve 117 opens, thus affording communication between the central lumen 116 and a region exterior to the catheter. In particular, the valve leaflet 118 flexes or pivots at its proximal end 118a so that its distal end 118b is drawn inward (i.e., towards the lumen). In typical operation, this situation occurs in response to concomitant blood flow external to the catheter.

Those skilled in the art will appreciate that many structural alternatives can serve as the passageways and valve means, and the present invention is not restricted to any particular one. For example, the passageway and valve means could be formed from a caged ball, caged disc, multi-cuspid valve, or the like. In a preferred embodiment, however, each passageway/valve pair should operate independently of other pairs so that a blockage at any one will not block others.

Figure 10:
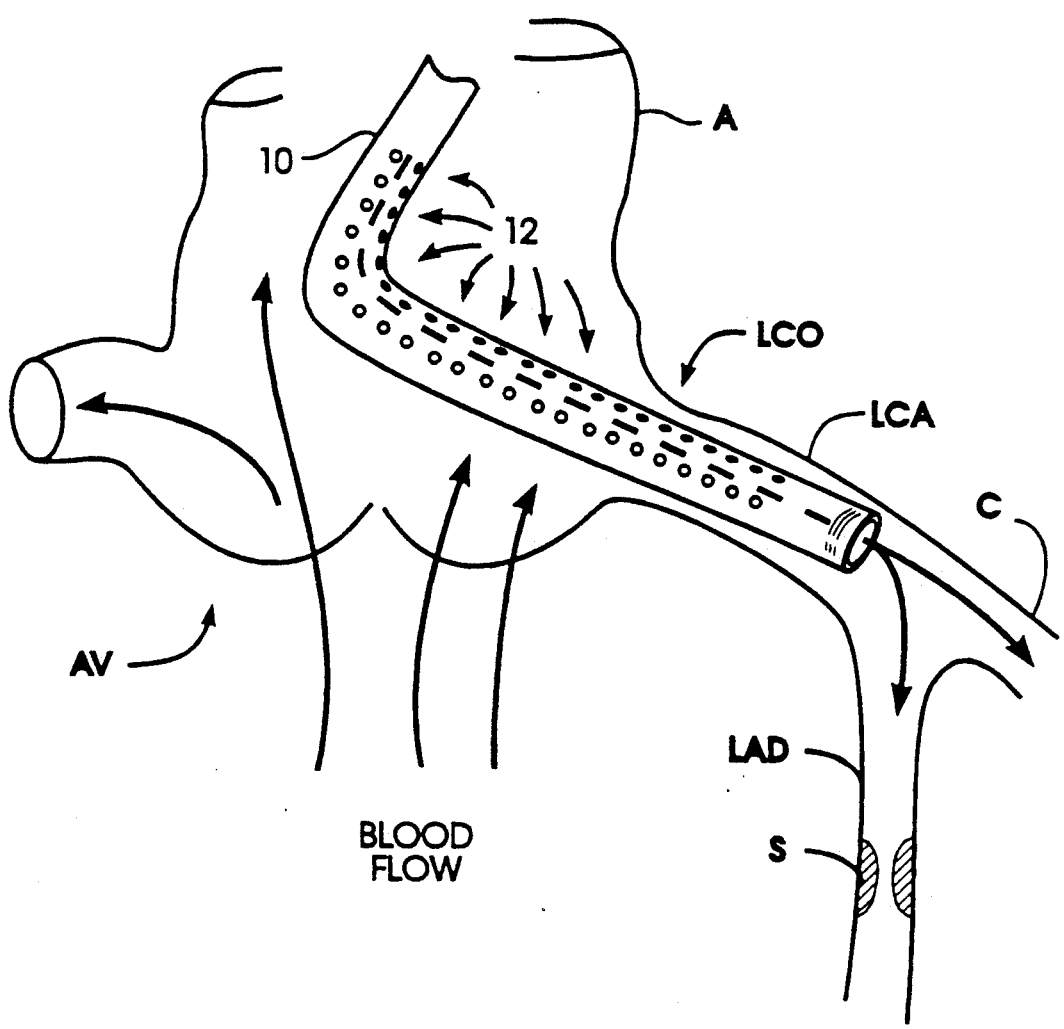
FIG. 10 illustrates a method of the present invention.

Referring now to FIG. 10, the use of the guiding catheter 10 of the present invention will now be described. The following discussion will focus on the treatment of a stenotic lesion within the left coronary artery using the apparatus and methods of the present invention. The present invention, however, is not limited to such treatment and may be employed advantageously to other regions within the coronary or systemic vascular system which require specific site treatment; examples include renal vasculature, upper and lower extremity vasculatures, and venae cava.

After initial preparation (e.g., saline flush), the guiding catheter 10 is percutaneously introduced into the patient's vascular system, typically employing conventional J-wire technique. Next, the guide is rotationally and translationally advanced. Under fluoroscopic guidance, the distal end of the guide may be positioned within the arch of the aorta A proximate the left coronary ostium LCO (just superior to the aortic (tricuspid) valve Av). By providing radio-opaque markers, typically located distally, fluoroscopic visualization is enhanced.

Next, the left coronary ostium LCO (or right ostium for right treatment) is cannulated by the guide 10, thus accessing the vessel of interest—the left main coronary artery LCA in this example. Once cannulated, however, the left ostium is at least partially blocked by the catheter; blood flow to the left coronary artery and its branches (left anterior descending LAD and circumflex C) is impeded. The provision of the passageways 12, however, channels blood flow from a region exterior to the catheter (e.g., aorta), through its central lumen, and cut through its distal end. Thus, perfusion is maintained.

In addition to unenhanced fluoroscopy, it may be desirable to image the lesion (e.g., stenosis S ) with a contrast media. In this case, contrast media is injected into the central lumen 116. During this and subsequent injections, the valves 17 occlude the passageways 12 so that the only communication between the central lumen 16 and a region exterior to the catheter is through the distal end 22. Hence, perfusion is maintained throughout the procedure and contrast media or other injectable agent (e.g., drug) is provided only to the vessel through the distal end 22.

After adequate imaging of the lesion, a second catheter (or other therapeutic modality) is inserted into the central lumen of the guiding catheter 10. For example, the second catheter may be a balloon-tipped angioplastic catheter delivered to the lesion through the lumen of the guiding catheter 10 for dilatating the stenosis.

In addition to facilitating angioplasty, catheter 10 may be employed advantageous for providing emergency perfusion of a desired vessel. Referring again to FIG. 10, catheter 10 may be positioned within the left main coronary artery LCA (as described hereinabove) for treating a dissected or closed left main coronary artery. With a plurality of passageways, such as circular side ports, the guide itself stents the left main coronary artery permitting sufficient perfusion of the distal vascular bed. When more definitive treatment (e.g., angioplasty) is available, the guide may be removed.

While the invention is described in some detail with specific reference to a single preferred embodiment and certain alternatives, there is no intent to limit the invention to that particular embodiment or those specific alternatives. For example, it will be apparent to those skilled in the art to apply the teachings of the present invention to other passageway/valve combinations. Therefore, the true scope of the invention is not defined by the foregoing description but by the following claims.

What is claimed is:

1. A perfusion guiding catheter comprising:
   an elongate, flexible catheter body having a proximal end, a distal end, and at least one lumen extending from the proximal end to the distal end and terminating in an open distal port;
   a plurality of radial passageways disposed along at least one region of the catheter body; and
   means operatively coupled to each passageway permitting unidirectional fluid flow from an exterior region into the lumen and outward through the open port in response to external pressure higher than lumen pressure.

2. The catheter of claim 1, wherein said passageways comprise a plurality of circular side holes disposed near the distal end of the catheter body.

3. The catheter of claim 1, wherein said passageways comprise a plurality of randomly configured holes disposed randomly along at least a portion of the catheter body.

4. The catheter of claim 1, wherein said means includes a unidirectional inlet valve leaflet attached at one end to an inner wall of the catheter body.

5. The catheter of claim 1, wherein said means includes a valve leaflet attached to an exterior wall of the catheter body.

6. The catheter of claim 5, wherein said exterior wall includes a recess for attaching a proximal end of the valve leaflet.

7. A perfusion guiding catheter comprising:
   an elongate a flexible catheter body having a proximal end, a distal end, and at least one lumen extending from the proximal end to the distal end;
   radial passageways, disposed along at least a portion of the catheter body, for permitting flow between said at least one lumen and an exterior region thereof, said passageways comprising a plurality of randomly configured holes disposed randomly along at least a portion of the catheter body; and
   means, operatively coupled to each of said passageways, for blocking flow between the lumen and the exterior region.

8. The catheter of claim 7, wherein said means is coupled to an inner wall of the catheter body.

9. The catheter of claim 7, wherein said means is coupled to an exterior wall of the catheter body.

10. The catheter of claim 7, wherein said means comprises a means for occluding said passageways in response to an intraluminal pressure higher than an external pressure.

11. A method for positioning a guiding catheter in a vessel, said method comprising:
    introducing a guiding catheter to the vessel, said guiding catheter including radial passageways for permitting blood flow through a central lumen of the catheter;
    injecting an agent into the central lumen, whereby valve means operably coupled to each passageway are closed by an increased intraluminal pressure; and
    stopping the injection of agent, whereby said valve means are opened by a decreased intraluminal pressure.

12. The method of claim 11, wherein said injected agent includes contrast media.

13. The method of claim 11, wherein said injected agent includes a drug.

14. The method of claim 11, further comprising the step of inserting a therapeutic catheter into the central lumen of said guiding catheter.

15. A method for stenting a vessel having a lesion, the method comprising:

introducing a guiding catheter to the vessel, said guiding catheter having a proximal end, a distal end, a lumen extending from the proximal end to the distal end, and passageways through at least one region thereof;

injecting a contrast media into the lumen for visualizing the lesion while said passageways are blocked to inhibit loss of media; and positioning the distal end of the catheter proximate the lesion while said passageways are unblocked to permit fluid flow from the vessel into the lumen.

16. The method of claim 15, further comprising:
introducing a therapeutic catheter to the lesion through the lumen of the guiding catheter.

17. A perfusion guiding catheter comprising:

an elongate, flexible catheter body having a proximal end, a distal end, and at least one lumen extending from the proximal end to the distal end and terminating in an open distal port;

a plurality of radial passageways disposed along at least one region of the catheter body; and means operatively coupled to each passageway permitting unidirectional fluid flow from an exterior region through the passageway into the lumen and outward through the open port and preventing flow from the lumen through the passageway to the exterior in response to an external pressure higher than lumen pressure, whereby bypass blood flow can be established from the exterior and through the lumen.

18. The catheter of claim 17, wherein said passageways comprise a plurality of circular side holes disposed near the distal end of the catheter body.

19. The catheter of claim 17, wherein said passageways comprise a plurality of randomly configured holes disposed randomly along at least a portion of the catheter body.

20. The catheter of claim 17, wherein said means includes a unidirectional inlet valve leaflet attached to an inner wall of the catheter body.

21. The catheter of claim 17, wherein said means includes a valve leaflet attached to an exterior wall of the catheter body.

22. The catheter of claim 21, wherein said exterior wall includes a recess for attaching a proximal end of the valve leaflet.

* * * * *